(12) United States Patent
Chen et al.

(10) Patent No.: US 10,487,064 B1
(45) Date of Patent: Nov. 26, 2019

(54) CRYSTALLINE FORMS OF SELECTIVE S1P1 RECEPTOR MODULATOR AND PREPARATION METHOD THEREOF

(71) Applicant: Crystal Pharmatech Co., Ltd., Suzhou, Jiangsu (CN)

(72) Inventors: Minhua Chen, Suzhou (CN); Yanfeng Zhang, Suzhou (CN); Jiaoyang Li, Suzhou (CN); Xiaoyu Zhang, Suzhou (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 34 days.

(21) Appl. No.: 16/065,350

(22) PCT Filed: Dec. 23, 2016

(86) PCT No.: PCT/CN2016/111689
§ 371 (c)(1),
(2) Date: Jun. 22, 2018

(87) PCT Pub. No.: WO2017/107972
PCT Pub. Date: Jun. 29, 2017

(30) Foreign Application Priority Data

Dec. 25, 2015 (CN) .......................... 2015 1 0993103

(51) Int. Cl.
*C07D 277/42* (2006.01)
*A61P 17/06* (2006.01)

(52) U.S. Cl.
CPC ............ *C07D 277/42* (2013.01); *A61P 17/06* (2018.01); *C07B 2200/13* (2013.01)

(58) Field of Classification Search
None
See application file for complete search history.

(56) References Cited

U.S. PATENT DOCUMENTS

| 2011/0196004 A1 | 8/2011 | Bonham et al. |
| 2015/0203459 A1 | 7/2015 | Herse |

FOREIGN PATENT DOCUMENTS

| CN | 1882555 A | 12/2006 |
| CN | 102177144 A | 9/2011 |
| CN | 104540800 A | 4/2015 |
| JP | 2012-505873 A | 3/2012 |
| JP | 2015-530373 A | 10/2015 |

OTHER PUBLICATIONS

Asahara et al., Solvent Utilization in Crystallization. pp. 46-51, (1976).
Bavin, Polymorphism in Process Development. Process Development Chemistry & Industry. Aug. 21, 1989, pp. 527-529.
Caira, Crystalline Polymorphism of Organic Compounds. Topics in Current Chemistry. 1998;198:163-208.
Kaneniwa et al., The Solubility, Dissolution Rate and Dissolution Rate Constant of Polymorphs of Some Crystalline Drugs. Calculation Methods of the Solubility and Dissolution Rate Constant of Metastable Forms Using Stable Form Data. The Society of Powder Technology. 1990;27(11):730-738.
Kawaguchi et al., Drug and crystal polymorphism Journal of Human Environmental Engineering. 2002;4(2):310-317.
Matsuda et al., Problems surrounding the formulation of polymorphism drugs. The Society of Powder Technology. 1984;21(11):704-714.
Yamano, Approach to crystal polymorph in process research of new drug. Journal of Synthetic Organic Chemistry. 2007;65(9):907-913.
Yuming, Organic Compound Crystallization Handbook and Principles. Part 2-Crystallization theory, Part 3-General method of crystallization, Part 4—Pharmaceutical crystallization. 28 pages, (2008).

*Primary Examiner* — Alicia L Otton
(74) *Attorney, Agent, or Firm* — McCarter & English, LLP; Steven G. Davis; Wei Song

(57) ABSTRACT

The present disclosure relates to crystalline Form 1, Form 2, Form 3 of Ponesimod, a selective S1P1 receptor modulator, and preparation methods thereof. The X-ray powder diffraction pattern of Form 1 shows characteristic peaks at 2theta values of 18.1°±0.2°, 14.6°±0.2°, 11.3°±0.2°; the X-ray powder diffraction pattern of Form 2 shows characteristic peaks at 2theta values of 3.8°±0.2°, 10.8°±0.2°, 6.1°±0.2°; the X-ray powder diffraction pattern of Form 3 shows characteristic peaks at 2theta values of 12.2°±0.2°, 6.2°±0.2°, 5.6°±0.2°. The crystalline forms in present disclosure not only have better stability but also have higher solubility compared with the prior art forms, they are more suitable for the formulation development of Ponesimod.

20 Claims, 5 Drawing Sheets

CRYSTALLINE FORMS OF SELECTIVE S1P1 RECEPTOR MODULATOR AND PREPARATION METHOD THEREOF

CROSS-REFERENCE TO RELATED APPLICATIONS

The present application is a U.S. national stage application, filed under 35 U.S.C. § 371(c), of International Application No. PCT/CN2016/111689, filed on Dec. 23, 2016, which claims the priority of Chinese Application No. 201510993103.7, filed on Dec. 25, 2015. The entire contents of the aforementioned application are incorporated herein by reference.

TECHNICAL FIELD

The present disclosure relates to the field of pharmaceutical chemistry, particularly relates to crystalline forms of Ponesimod, a selective S1P1 receptor modulator and preparation method thereof.

BACKGROUND

It is generally known that crystalline forms greatly affect drug's quality. Different crystalline forms may have remarkable difference in appearance, solubility, melting point, dissolution profile, bioavailability and so on, thus affect drug's stability, bioavailability and efficacy. Therefore, it is of great significance to develop novel and more suitable crystalline forms for drug development.

Ponesimod (Compound I) is a selective S1P1 receptor modulator developed by Actelion. The drug achieved positive results in phase II mid-stage study for the treatment of moderate-to-severe chronic plaque psoriasis, and will be studied in phase III for the treatment of psoriasis.

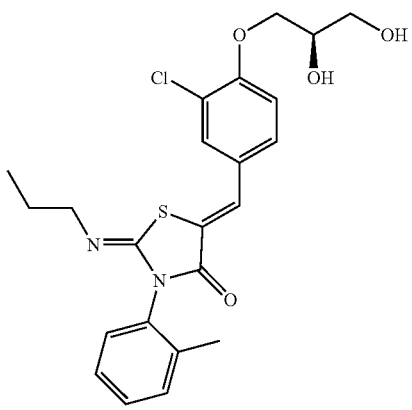

(I)

At present, CN100567275 C discloses a preparation method of Compound I in example 85, which is amorphous according to disclosure of CN102177144 B.

Additionally CN102177144 B discloses Form A, Form C, Form III and Form II of Compound I. Studies show that Form III has poor crystallinity, and will transform to Form II at room temperature; Form II is difficult to repeat and contains a certain amount of propionic acid; thermodynamic stability of Form A is inferior to Form C. Compared with them all, Form C is suitable for drug development, but its solubility is unsatisfactory.

SUMMARY

To solve the problems of prior art, the objective of the present disclosure is to provide crystalline forms of Ponesimod with better properties than Form C in prior art, and these crystalline forms are designated as Form 1, Form 2, and Form 3.

The present disclosure also provides the preparation method and use of Form 1, Form 2, and Form 3.

The X-ray powder diffraction pattern of Form 1 of present disclosure shows characteristic peaks at 2theta values of 18.1°±0.2°, 14.6°±0.2°, 11.3°±0.2°.

Furthermore, the X-ray powder diffraction pattern of Form 1 further shows one or more characteristic peaks at 2theta values of 10.8°±0.2°, 16.3°±0.2°, 22.7°±0.2°. Preferably, the X-ray powder diffraction pattern of Form 1 shows characteristic peaks at 2theta values of 10.8°±0.2°, 16.3°±0.2°, 22.7°±0.2°.

Furthermore, the X-ray powder diffraction pattern of Form 1 further shows one or more characteristic peaks at 2theta values of 26.0°±0.2°, 6.8°±0.2°, 13.1°±0.2°. Preferably, the X-ray powder diffraction pattern of Form 1 shows diffraction peaks at 2theta values of 26.0°±0.2°, 6.8°±0.2°, 13.1°±0.2°.

According to a specific and preferred aspect of the present disclosure, the X-ray powder diffraction pattern of Form 1 is substantially as depicted in FIG. 1.

Preferably, Form 1 of present disclosure shows an endothermic peak when heated to around 78° C. (onset temperature), and the differential scanning calorimetry (DSC) curve is substantially as depicted in FIG. 2.

Preferably, Form 1 of present disclosure shows 7.1% weight loss when heated to 100° C., and the thermal gravimetric analysis (TGA) curve is substantially as depicted in FIG. 3.

The preparation method of Form 1 comprises: dissolving Ponesimod into cyclic ethers to obtain a solution, and then adding alkanes into the solution until solid is precipitated out and Form 1 is obtained.

Furthermore, said cyclic ethers include, but not limited to one or more solvents selected from tetrahydrofuran, 1,4-dioxane and the like. Preferably, said cyclic ether is 1,4-dioxane. Said alkanes include, but not limited to one or more solvents selected from n-hexane, n-heptane and the like. Preferably, said alkane is n-heptane.

The X-ray powder diffraction pattern of Form 2 of the present disclosure shows characteristic peaks at 2theta values of 3.8°±0.2°, 10.8°±0.2°, 6.1°±0.2°.

Furthermore, the X-ray powder diffraction pattern of Form 2 further shows one or more diffraction peaks at 2theta values of 5.4°±0.2°, 10.2°±0.2°, 7.0°±0.2°. Preferably, the X-ray powder diffraction pattern of Form 2 shows diffraction peaks at 2theta values of 5.4°±0.2°, 10.2°±0.2°, 7.0°±0.2°.

Furthermore, the X-ray powder diffraction pattern of Form 2 further shows one or more diffraction peaks at 2theta values of 13.7°±0.2°, 7.6°±0.2°, 11.4°±0.2°. Preferably, the X-ray powder diffraction pattern of Form 2 shows diffraction peaks at 2theta values of 13.7°±0.2°, 7.6°±0.2°, 11.4°±0.2°.

According to a specific and preferred aspect of the present disclosure, the X-ray powder diffraction pattern of Form 2 is substantially as depicted in FIG. 4.

Preferably, Form 2 of the present disclosure shows an endothermic peaks when heated to around 88° C. (onset temperature), and the differential scanning calorimetry (DSC) curve is substantially as depicted in FIG. 5.

Form 2 of the present disclosure shows 1.4% weight loss when heated to 80° C., and the thermal gravimetric analysis (TGA) curve is substantially as depicted in FIG. 6.

The preparation method of Form 2 comprises: mixing Ponesimod with esters to obtain a suspension, and stirring the suspension at a temperature of 0-50° C., isolating solid to obtain Form 2 of Ponesimod.

Furthermore, said esters include, but not limited to one or more solvents selected from isopropyl acetate, ethyl acetate and the like. Preferably, said ester is isopropyl acetate or ethyl acetate.

Preferably, the preparation method of Form 2 comprises stirring the suspension at room temperature.

The X-ray powder diffraction pattern of Form 3 of the present disclosure shows characteristic peaks at 2theta values of 12.2°±0.2°, 6.2°±0.2°, 5.6°±0.2°.

Furthermore, the X-ray powder diffraction pattern of Form 3 shows one or more diffraction peaks at 2theta values of 10.8°±0.2°, 13.4°±0.2°, 11.2°±0.2°. Preferably, the X-ray powder diffraction pattern of Form 3 shows diffraction peaks at 2theta values of 10.8°±0.2°, 13.4°±0.2°, 11.2°±0.2°.

Furthermore, the X-ray powder diffraction pattern of Form 3 shows one or more diffraction peaks at 2theta values of 10.2°±0.2°, 16.3°±0.2°, 20.5°±0.2°. Preferably, the X-ray powder diffraction pattern of Form 3 shows diffraction peaks at 2theta values of 10.2°±0.2°, 16.3°±0.2°, 20.5°±0.2°.

According to a specific and preferred aspect of the present disclosure, the X-ray powder diffraction pattern of Form 3 is substantially as depicted in FIG. 7.

Preferably, Form 3 of the present disclosure shows an endothermic peak when heated to around 85° C. (onset temperature), and the differential scanning calorimetry (DSC) curve is substantially as depicted in FIG. 8.

Form 3 can be prepared by any one of the following preparation methods:
1) mixing Ponesimod with esters, heating the mixture to obtain a clear solution, cooling until solid is precipitated out, isolating the solid to obtain Form 3. Said esters include, but not limited to isopropyl acetate, ethyl acetate and the like. Preferably the ester is isopropyl acetate or ethyl acetate; said mixture is heated to 40-80° C. in the heating process, more preferably 50-80° C., most preferably 50-60° C.; said mixture is preferably cooled to −5° C.-5° C. in the cooling process, more preferably about 4° C.
2) mixing Ponesimod with ethers to obtain a suspension and stirring the suspension at a temperature of 40-60° C., isolating the solid to obtain Form 3. Said ethers include, but not limited to methyl tert-butyl ether.

Form 1, Form 2, Form 3 or their mixture in any ratio can be used as a selective S1P1 receptor modulator for preparing drugs for treatment of psoriasis.

The present disclosure also relates to a pharmaceutical composition comprising Form 1, Form 2, Form 3 or their mixture in any ratio. Furthermore, the pharmaceutical composition can be used for treatment of psoriasis, including but not limited to treatment of moderate-to-severe chronic plaque psoriasis and the like.

By carrying out the above-mentioned technical solution, the present disclosure has the following advantages over prior art:

Form 1, Form 2 and Form 3 of Ponesimod in the present disclosure are surprisingly discovered, which have better stability and solubility than Form C in prior art. The present disclosure provides new and better choices for the formulation development of Ponesimod, and is of great significance to drug development.

DETAILED DESCRIPTION OF THE DISCLOSURE

The present disclosure will be further explained by the specific examples, but the present disclosure is not limited to the following examples. The experimental conditions not specified are general conditions. Starting material of Ponesimod used in the preparation method is amorphous prepared by known method in prior art (for example, the method disclosed in CN100567275 C or CN102177144 B).

In the following examples, general conditions or conditions recommended by the manufacturer are used in test methods.

The abbreviations in the present disclosure are explained as follows:

XRPD: X-ray Powder Diffraction;
DSC: Differential Scanning calorimetry;
TGA: Thermal Gravimetric Analysis.

X-ray powder diffraction pattern in the present disclosure was acquired by a Panalytical Empyrean X-ray powder diffractometer. The parameters of the X-ray powder diffraction of the present disclosure are as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scanning range: from 3.0 degree to 40.0 degree Differential scanning calorimetry (DSC) data in the present disclosure were acquired by a TA Q2000. The parameters of the differential scanning calorimetry (DSC) method of the present disclosure were as follows:

Heating rate: 10° C./min
Purge gas: nitrogen

Thermal gravimetric analysis (TGA) data in the present disclosure are acquired by a TA Q5000. The parameters of the thermal gravimetric analysis (TGA) method of the present disclosure were as follow:

Heating rate: 10° C./min
Purge gas: nitrogen

Example 1

Preparation Method of Form 1:

48.1 mg of Ponesimod was added into 0.4 mL of 1,4-dioxane, then the mixture was filtered to obtain a filtrate. 1.2 mL of n-heptane was added dropwise into the filtrate at room temperature to obtain a suspension, then the suspension was stirred overnight and Form 1 was obtained by centrifugation.

Figure 1:
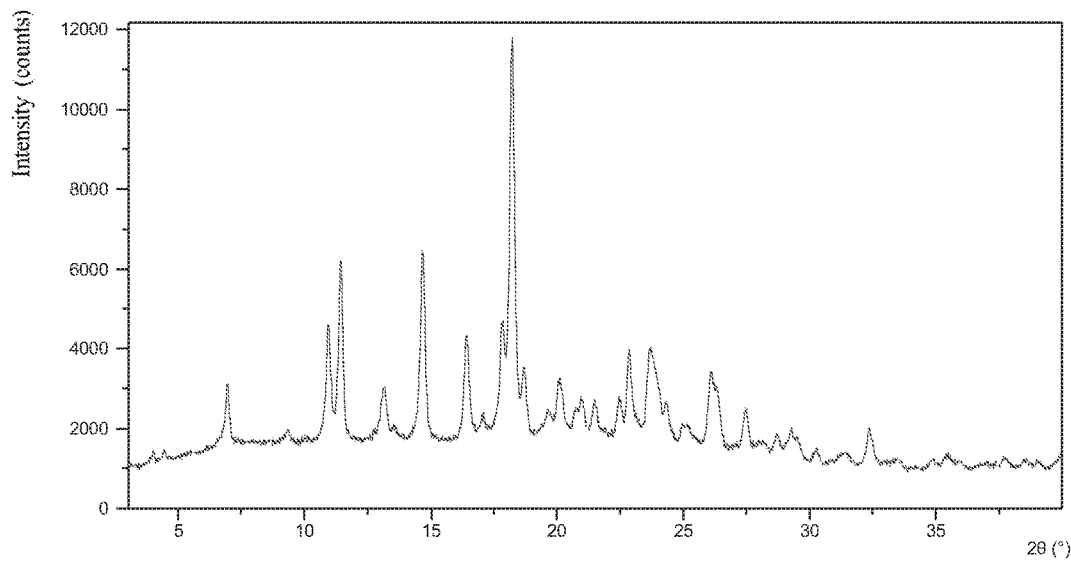
FIG. 1 shows an XRPD pattern of Form 1.
Figure 2:
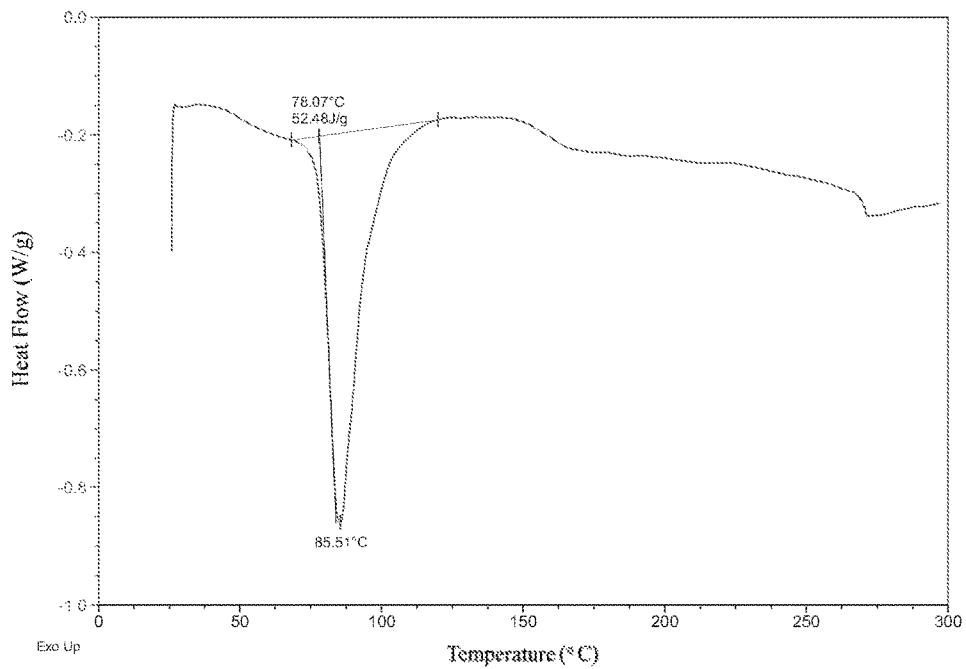
FIG. 2 shows a DSC curve of Form 1.
Figure 3:
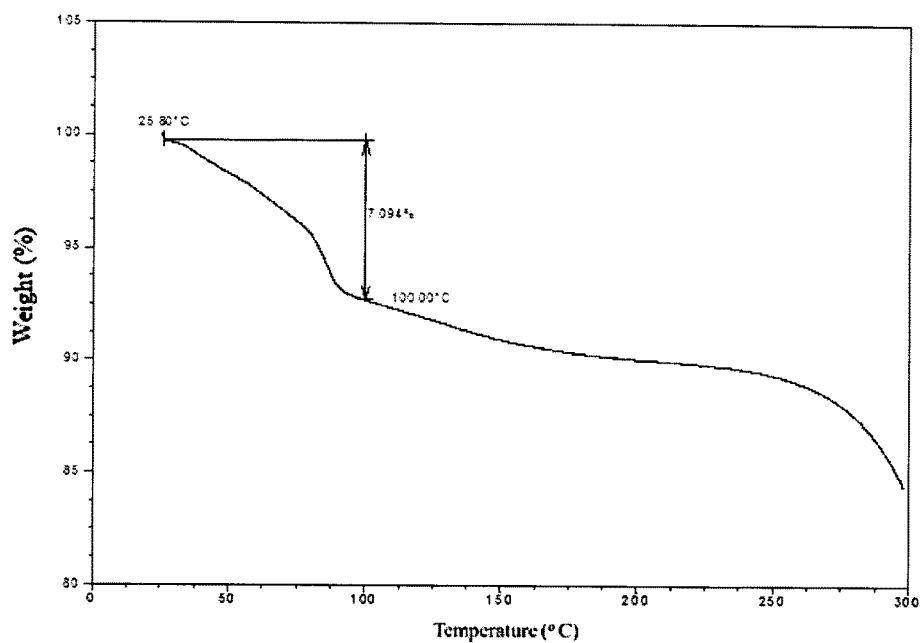
FIG. 3 shows a TGA curve of Form 1.

The XRPD data of Form 1 prepared in this example comprise diffraction peaks listed in Table 1. The XRPD pattern is displayed in FIG. 1. The DSC curve is displayed in FIG. 2. The TGA curve is displayed in FIG. 3.

TABLE 1

| 2theta | d spacing | intensity % |
|---|---|---|
| 3.90 | 22.63 | 3.82 |
| 4.33 | 20.38 | 4.11 |
| 6.83 | 12.95 | 19.68 |
| 9.25 | 9.56 | 8.92 |
| 10.83 | 8.17 | 33.57 |
| 11.33 | 7.81 | 48.18 |
| 13.07 | 6.78 | 18.63 |
| 14.55 | 6.09 | 50.30 |
| 16.28 | 5.44 | 30.46 |
| 16.95 | 5.23 | 12.05 |
| 17.69 | 5.01 | 33.34 |
| 18.10 | 4.90 | 100.00 |
| 18.62 | 4.76 | 21.41 |
| 19.54 | 4.54 | 13.20 |
| 20.02 | 4.44 | 20.89 |
| 20.89 | 4.25 | 15.98 |
| 21.39 | 4.15 | 15.31 |
| 22.37 | 3.97 | 15.94 |
| 22.74 | 3.91 | 26.48 |
| 23.56 | 3.78 | 27.53 |
| 24.20 | 3.68 | 15.26 |
| 24.86 | 3.58 | 10.25 |
| 25.04 | 3.56 | 9.56 |
| 25.96 | 3.43 | 21.58 |
| 26.24 | 3.40 | 18.40 |
| 27.36 | 3.26 | 13.49 |
| 28.06 | 3.18 | 5.96 |
| 28.61 | 3.12 | 7.59 |
| 29.16 | 3.06 | 9.02 |
| 30.16 | 2.96 | 4.41 |
| 31.36 | 2.85 | 3.55 |
| 32.26 | 2.78 | 9.03 |
| 35.32 | 2.54 | 2.65 |

Example 2

Preparation Method of Form 2:

399.9 mg of Ponesimod was added into 4.0 mL of ethyl acetate to obtain a suspension. The obtained suspension was stirred at room temperature for 24 hours, and then centrifuged to obtain a solid. The obtained solid was dried under vacuum for 3 hours at room temperature. The obtained solid was Form 2.

Figure 5:
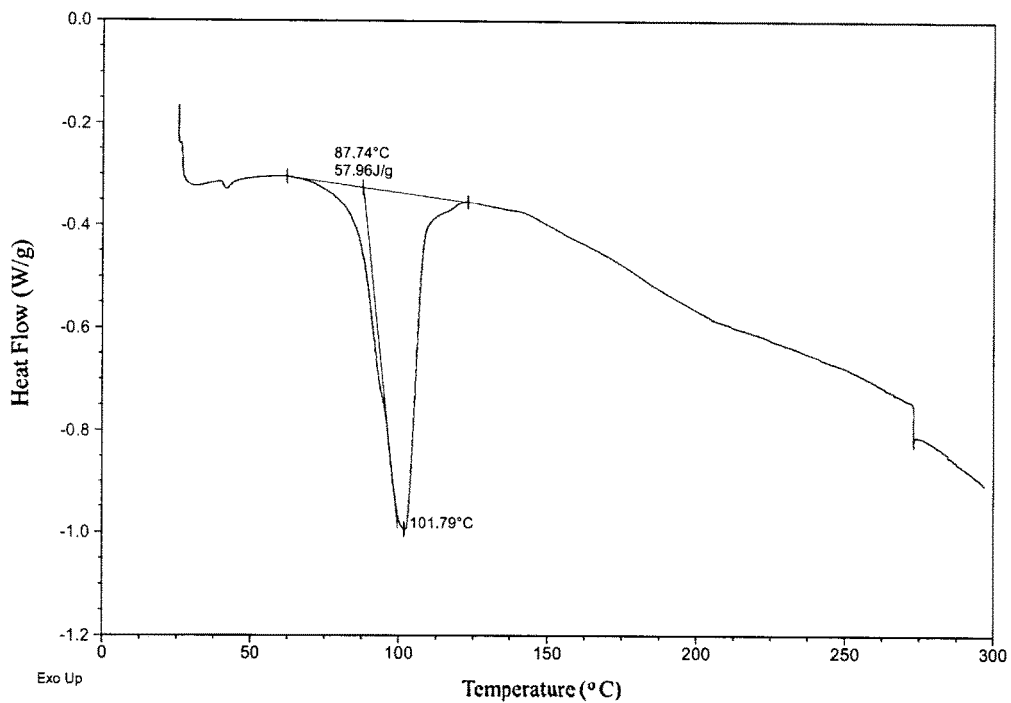
FIG. 5 shows a DSC curve of Form 2.
Figure 6:
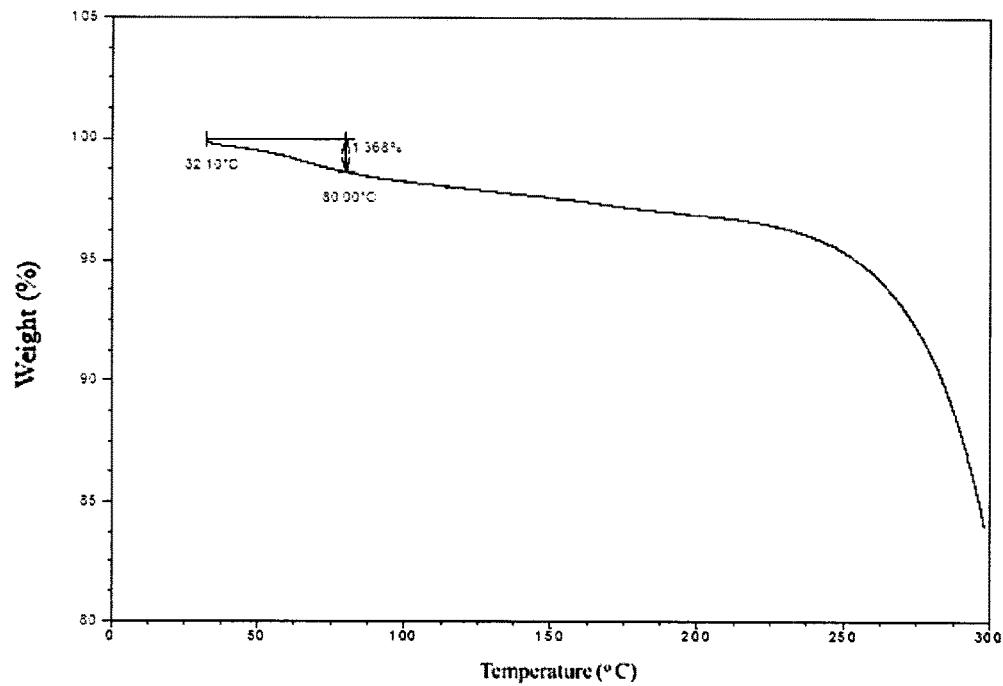
FIG. 6 shows a TGA curve of Form 2.

The XRPD data of Form 2 prepared in this example comprise the diffraction peaks listed in Table 2. The XRPD pattern is displayed in FIG. 4. The DSC curve is displayed in FIG. 5. The TGA curve is displayed in FIG. 6.

TABLE 2

| 2theta | d spacing | Intensity % |
|---|---|---|
| 3.83 | 23.05 | 100.00 |
| 5.39 | 16.40 | 57.99 |
| 6.13 | 14.42 | 61.47 |
| 7.01 | 12.61 | 51.80 |
| 7.61 | 11.62 | 31.18 |
| 8.70 | 10.17 | 18.02 |
| 9.13 | 9.68 | 16.66 |
| 9.60 | 9.22 | 16.67 |
| 10.19 | 8.68 | 55.67 |
| 10.76 | 8.22 | 68.96 |
| 11.42 | 7.75 | 30.04 |
| 12.04 | 7.35 | 20.31 |
| 12.33 | 7.18 | 16.82 |
| 12.94 | 6.84 | 21.97 |
| 13.69 | 6.47 | 50.85 |
| 14.64 | 6.05 | 19.98 |
| 15.23 | 5.82 | 3.84 |
| 17.04 | 5.20 | 19.88 |
| 18.81 | 4.72 | 21.25 |
| 20.52 | 4.33 | 10.78 |
| 22.23 | 4.00 | 21.07 |
| 23.88 | 3.73 | 13.89 |
| 24.26 | 3.67 | 14.97 |
| 25.86 | 3.45 | 9.12 |
| 29.93 | 2.99 | 1.31 |

Example 3

Preparation Method of Form 3:

106.8 mg of Ponesimod was added into 2.0 mL of methyl tert-butyl ether to obtain a suspension. The obtained suspension was stirred at 50° C. for 24 hours, and then centrifuged to obtain a solid. The obtained solid was dried under vacuum for 3 hours at room temperature. The obtained solid was Form 3 of Ponesimod.

The XRPD data of Form 3 prepared in this example comprise the diffraction peaks listed in Table 3. The XRPD pattern is displayed in FIG. 7. The DSC curve is displayed in FIG. 8.

TABLE 3

| 2theta | d spacing | Intensity % |
|---|---|---|
| 3.04 | 29.06 | 44.85 |
| 4.11 | 21.47 | 48.04 |
| 5.57 | 15.86 | 68.31 |
| 6.22 | 14.21 | 100.00 |
| 6.80 | 13.00 | 35.35 |
| 7.12 | 12.42 | 34.38 |
| 8.24 | 10.73 | 22.06 |
| 8.63 | 10.25 | 27.59 |
| 9.37 | 9.44 | 23.09 |
| 9.77 | 9.05 | 29.19 |
| 10.19 | 8.68 | 46.52 |
| 10.84 | 8.16 | 65.59 |
| 11.20 | 7.90 | 48.96 |
| 11.72 | 7.55 | 19.84 |
| 12.22 | 7.24 | 88.65 |
| 12.81 | 6.91 | 18.81 |
| 13.42 | 6.60 | 55.47 |
| 13.65 | 6.49 | 34.77 |
| 14.28 | 6.20 | 10.23 |
| 14.90 | 5.95 | 10.64 |
| 16.28 | 5.45 | 41.52 |
| 17.49 | 5.07 | 9.70 |
| 18.88 | 4.70 | 21.65 |
| 19.11 | 4.64 | 26.78 |
| 19.49 | 4.55 | 12.97 |
| 20.46 | 4.34 | 30.74 |
| 21.17 | 4.20 | 10.12 |
| 21.89 | 4.06 | 23.63 |
| 22.62 | 3.93 | 12.80 |
| 23.52 | 3.78 | 10.69 |
| 24.39 | 3.65 | 16.03 |

TABLE 3-continued

| 2theta | d spacing | Intensity % |
|---|---|---|
| 24.62 | 3.62 | 14.56 |
| 25.13 | 3.54 | 7.78 |
| 26.19 | 3.40 | 6.51 |
| 27.26 | 3.27 | 4.75 |

Example 4

Preparation Method of Form 3:

149.5 mg of Ponesimod was added into 1.2 mL of ethyl acetate to obtain a mixture. The mixture was heated to 50° C. to obtain a clear solution, and then the solution was cooled to 4° C. for crystallization, centrifuged to obtain a solid. The solid was dried under vacuum for 3 hours at room temperature. The obtained solid was Form 3 of Ponesimod.

The XRPD data of Form 3 prepared in this example comprise the diffraction peaks listed in Table 4.

TABLE 4

| 2theta | d spacing | Intensity % |
|---|---|---|
| 5.51 | 16.03 | 59.01 |
| 6.23 | 14.19 | 100.00 |
| 6.89 | 12.82 | 20.88 |
| 8.60 | 10.28 | 28.10 |
| 9.76 | 9.06 | 23.34 |
| 10.15 | 8.71 | 46.48 |
| 10.82 | 8.18 | 86.19 |
| 11.21 | 7.89 | 66.72 |
| 12.14 | 7.29 | 95.88 |
| 13.35 | 6.63 | 58.84 |
| 16.30 | 5.44 | 42.09 |
| 18.97 | 4.68 | 24.42 |
| 20.50 | 4.33 | 29.97 |
| 21.92 | 4.06 | 24.79 |
| 24.43 | 3.64 | 15.93 |

Example 5

Figure 9:
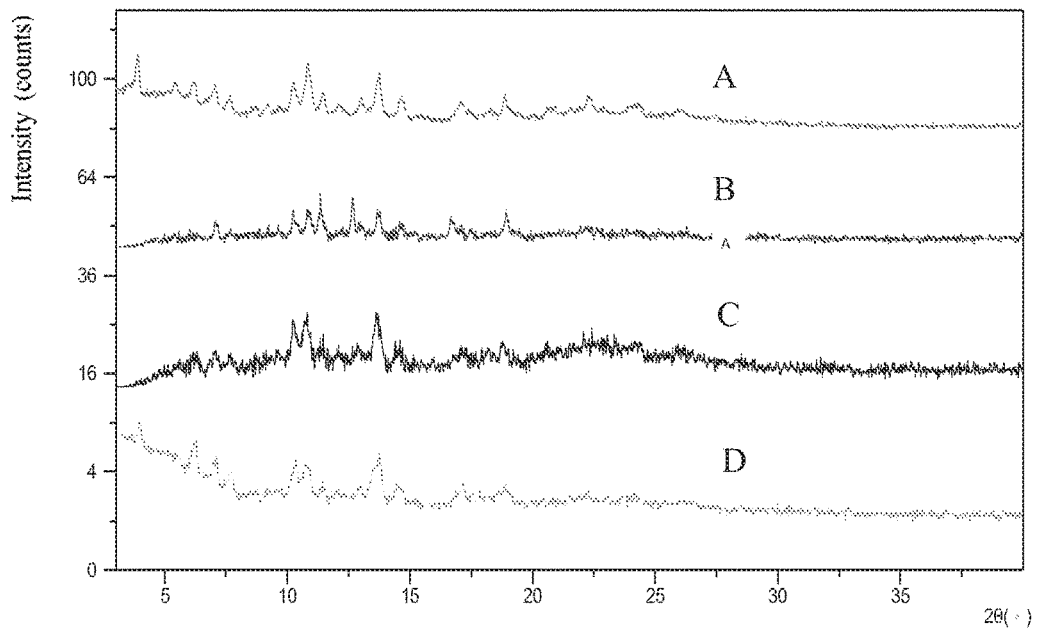
FIG. 9 shows an XRPD overlay pattern of Form 2 before and after storage (A is the sample before storage, B is the sample after stored under 25° C./60% RH for 6 months, C is the sample after stored under 40° C./75% RH for 6 months, D is the sample after stored under 80° C. for 3 months)

Stability Assessment of Form 2:

20 mg of sample of Form 2 was stored under 25° C./60% RH, 40° C./75% RH for 6 months, and 80° C. for 3 months. The assessment results were shown in Table 5. The XRPD patterns of Form 2 before and after storage were depicted in FIG. 9, which show that Form 2 sample doesn't change under 25° C./60% RH and 40° C./75% RH for 6 months, under 80° C. for 3 months. The results indicate that Form 2 has good physical stability.

TABLE 5

Stability assessment of Form 2

| Initial Form | Conditions | Storage time | Solid Form after storage |
|---|---|---|---|
| Form 2 (FIG. 9A) | 25° C./60% RH | 6 months | Form 2 (FIG. 9B) |
| Form 2 (FIG. 9A) | 40° C./75% RH | 6 months | Form 2 (FIG. 9C) |
| Form 2 (FIG. 9A) | 80° C. | 3 months | Form 2 (FIG. 9D) |

Example 6

Figure 10:
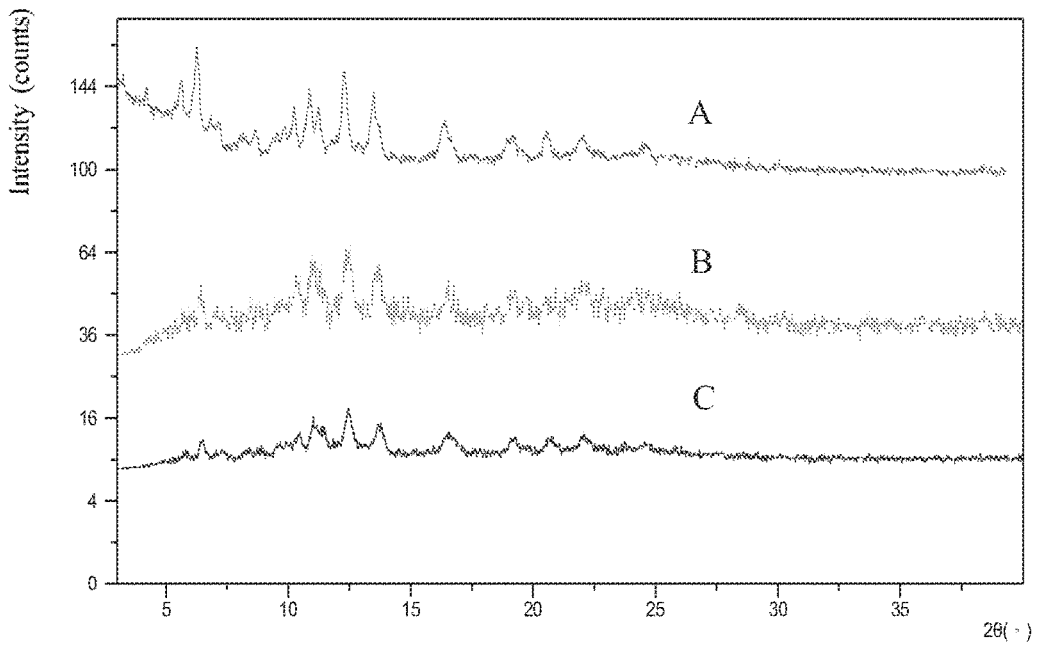
FIG. 10 shows an XRPD overlay pattern of Form 3 before and after storage (A is the sample before storage, B is the sample after stored under 25° C./60% RH for 6 months, C is the sample after stored under 40° C./75% RH for 6 months).

Stability Assessment of Form 3:

20 mg of sample of Form 3 was stored under 25° C./60% RH and 40° C./75% RH for 6 months. The assessment results were shown in Table 6. The XRPD patterns of Form 3 before and after storage were depicted in FIG. 10, which show that Form 3 doesn't change under 25° C./60% RH and 40° C./75% RH for 6 months. The results indicate that Form 3 has good physical stability.

TABLE 6

Stability assessment of Form 3

| Initial form | Conditions | Storage time | Crystalline form after storing |
|---|---|---|---|
| Form 3 (FIG. 10A) | 25° C./60% RH | 6 months | Form 3 (FIG. 10B) |
| Form 3 (FIG. 10A) | 40° C./75% RH | 6 months | Form 3 (FIG. 10C) |

Example 7

Solubility assessment of Form 2 in present disclosure and Form A, Form C disclosed in CN102177144B:

Saturated solution of Form 2 and Form A, Form C disclosed in CN102177144B were prepared in FaSSIF (Fasted state simulated intestinal fluids, pH=6.5), FeSSIF (Fed state simulated intestinal fluids, pH=5.0), SGF (Simulated gastric fluids, pH=1.8), and water. Concentrations in the saturation solutions were measured after 1 hour and 24 hours by HPLC. The data were listed in Table 7.

TABLE 7

Solubility of Form 2 and Form A, Form C disclosed in CN102177144B

| | | FaSSIF | | | FeSSIF | | | SGF | | | H$_2$O | | |
|---|---|---|---|---|---|---|---|---|---|---|---|---|---|
| | Time | Form A | Form C | Form 2 | Form A | Form C | Form 2 | Form A | Form C | Form 2 | Form A | Form C | Form 2 |
| Solubility (mg/mL) | 1 h | 0.007 | 0.010 | 0.017 | 0.141 | 0.133 | 0.996 | 0.034 | 0.029 | 0.097 | ND* | 0.003 | ND |
| | 24 h | 0.004 | 0.003 | 0.033 | 0.163 | 0.149 | 0.813 | 0.045 | 0.024 | 0.124 | ND | 0.001 | ND |

*ND: below the LOD of instrument

The data in Table 7 indicate that the solubility of Form 2 is higher than that of Form A and Form C in FaSSIF, FeSSIF, and SGF, which means Form 2 will have higher bioavailability, which is of great significance to improve the efficacy and safety of Ponesimod and reduce the drug loading.

Example 8

Solubility assessment of Form 3 and Form A, Form C:

Form 3 and Form A, Form C were prepared into saturated solution in FaSSIF (Fasted state simulated intestinal fluids, pH=6.5), FeSSIF (Fed state simulated intestinal fluids, pH=5.0) and water. Concentrations in the saturation solutions were measured after 1 hour and 24 hours by HPLC. The results were listed in Table 8.

TABLE 8

Solubility of Form 3 and Form A, Form C disclosed in CN102177144B.

|  |  | FaSSIF |  |  | FeSSIF |  |  | H$_2$O |  |  |
|---|---|---|---|---|---|---|---|---|---|---|
|  | Time | Form A | Form C | From 3 | From A | From C | From 3 | From A | From C | From 3 |
| Solubility (mg/mL) | 1 h | 0.007 | 0.010 | 0.084 | 0.141 | 0.133 | 1.168 | ND* | 0.003 | ND |
|  | 24 h | 0.004 | 0.003 | 0.015 | 0.163 | 0.149 | 0.486 | ND | 0.001 | ND |

*ND: below the LOD of instrument

Solubility is one of the key characteristics of a drug, which directly affects in vivo absorption of the drug. Different crystalline forms have remarkable difference in solubility, and will affect in vivo absorption, thus lead to the differences in bioavailability. As a result, clinical safety and efficacy will be affected.

The data in Table 8 indicate that the solubility of Form 3 is higher than that of Form A and Form C in FaSSIF and FeSSIF, which means Form 3 will have higher bioavailability, which is of great significance to improve the efficacy and safety of Ponesimod and reduce the drug loading.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline Form 2 of Ponesimod, wherein the X-ray powder diffraction pattern (CuKα radiation) shows characteristic peaks at 2theta values of 3.8°±0.2°, 10.8°±0.2°, and 6.1°±0.2°.

2. The crystalline Form 2 according to claim 1, wherein the X-ray powder diffraction pattern further shows one or more characteristic peaks at 2theta values of 5.4°±0.2°, 10.2°±0.2°, and 7.0°±0.2°.

3. The crystalline Form 2 according to claim 1, wherein the X-ray powder diffraction pattern further shows one or more characteristic peaks at 2theta values of 13.7°±0.2°, 7.6°±0.2°, and 11.4°±0.2°.

Figure 4:
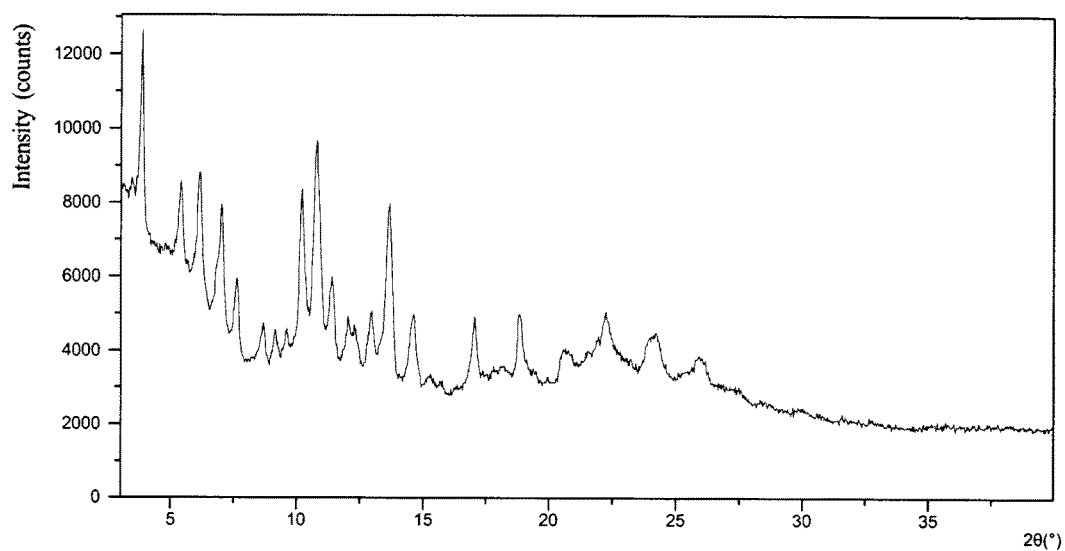
FIG. 4 shows an XRPD pattern of Form 2.

4. The crystalline Form 2 according to claim 1, wherein the X-ray powder diffraction pattern of Form 2 is substantially as depicted in FIG. 4.

5. A preparation method of Form 2 according to claim 1, wherein the method comprises: mixing Ponesimod with esters to obtain a suspension, and stirring the suspension at a temperature of 0-50° C., isolating solids to obtain Form 2.

6. The preparation method according to claim 5, wherein said ester is isopropyl acetate or ethyl acetate or a combination thereof.

7. A crystalline Form 3 of Ponesimod, wherein the X-ray powder diffraction pattern (CuKα radiation) shows characteristic peaks at 2theta values of 12.2°±0.2°, 6.2°±0.2°, and 5.6°±0.2°.

8. The crystalline Form 3 according to claim 7, wherein the X-ray powder diffraction pattern further shows one or more characteristic peaks at 2theta values of 10.8°±0.2°, 13.4°±0.2°, and 11.2°±0.2°.

9. The crystalline Form 3 according to claim 7, wherein the X-ray powder diffraction pattern further shows one or more characteristic peaks at 2theta values of 10.2°±0.2°, 16.3°±0.2°, and 20.5°±0.2°.

Figure 7:
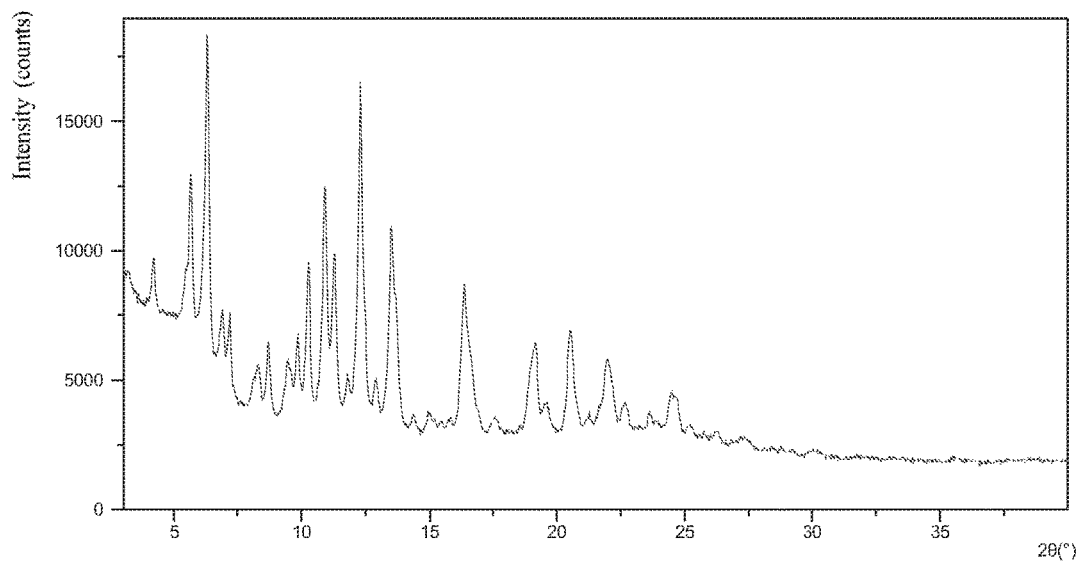
FIG. 7 shows an XRPD pattern of Form 3.
Figure 8:
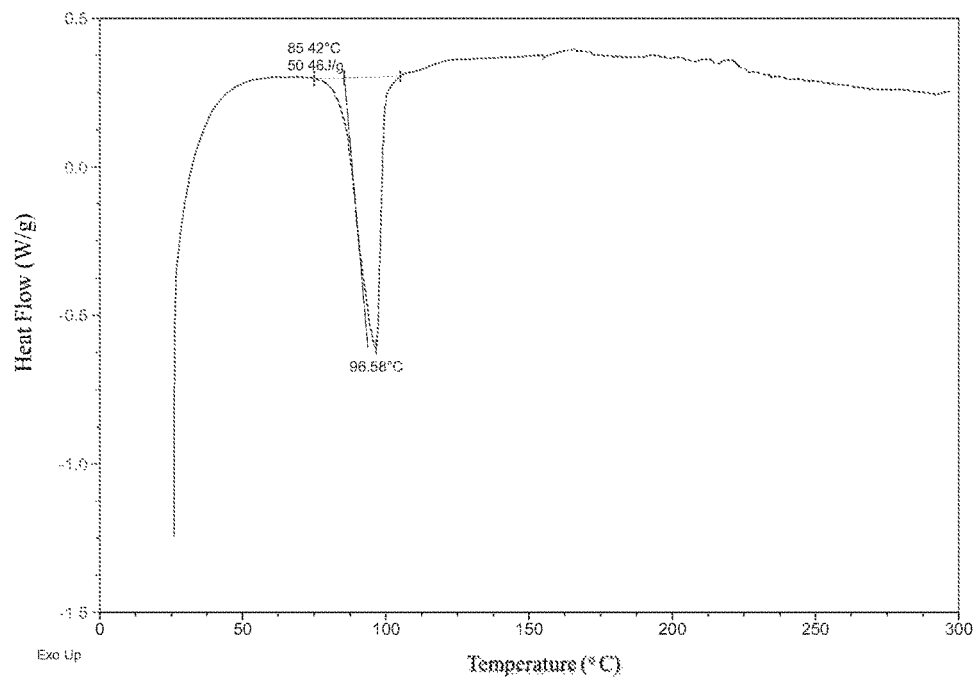
FIG. 8 shows a DSC curve of Form 3.

10. The crystalline Form 3 according to claim 7, wherein the X-ray powder diffraction pattern of Form 3 is substantially as depicted in FIG. 7.

11. A preparation method of Form 3 according to claim 7, wherein the method is method 1) or method 2):
  method 1) comprising mixing Ponesimod with esters and firstly heating the mixture to obtain a clear solution, and then cooling until solids are precipitated out, isolating the solids to obtain Form 3;
  method 2) comprising mixing Ponesimod with ethers to obtain a suspension and stirring the suspension at a temperature of 40-60° C., isolating solids to obtain Form 3.

12. The preparation method according to claim 11, wherein in method 1), said ester is isopropyl acetate or ethyl acetate or a combination thereof; in method 2), said ether is methyl tert-butyl ether.

13. The preparation method according to claim 11, wherein in the method 1), said mixture is heated to 40-80° C. in the heating process; said mixture is cooled to −5° C.-5° C. in the cooling process.

14. A crystalline Form 1 of Ponesimod, wherein the X-ray powder diffraction pattern (CuKα radiation) shows characteristic peaks at 2theta values of 18.1°±0.2°, 14.6°±0.2°, and 11.3°±0.2°.

15. The crystalline Form 1 according to claim 14, wherein the X-ray powder diffraction pattern further shows one or more of characteristic peaks at 2theta values of 10.8°±0.2°, 16.3°±0.2°, 22.7°±0.2°, 26.0°±0.2°, 6.8°±0.2°, and 13.1°±0.2°.

16. A preparation method of Form 1 according to claim 14, wherein the method comprises: dissolving Ponesimod into cyclic ethers to obtain a solution, and then adding alkanes into the solution until solids are precipitated out and Form I is obtained.

17. A pharmaceutical composition comprising a therapeutically effective amount of Ponesimod and pharmaceutically acceptable excipients, wherein said Ponesimod is Form 2 according to claim 1.

18. The pharmaceutical composition according to claim 17, wherein the pharmaceutical composition is used for treatment of psoriasis.

19. A pharmaceutical composition comprising a therapeutically effective amount of Ponesimod and pharmaceutically acceptable excipients, wherein said Ponesimod is Form 3 according to claim 7.

20. A pharmaceutical composition comprising a therapeutically effective amount of Ponesimod and pharmaceutically acceptable excipients, wherein said Ponesimod is Form 1 according to claim 14.

* * * * *